US009451875B2

(12) United States Patent
Sigmon, Jr. et al.

(10) Patent No.: US 9,451,875 B2
(45) Date of Patent: Sep. 27, 2016

(54) FLEXIBLE LENS (71) Applicant: Cook Medical Technologies LLC, Bloomington, IN (US)

(72) Inventors: John C. Sigmon, Jr., Winston-Salem, NC (US); Vihar Surti, Winston-Salem, NC (US); Michelle D. Martinez, Winston-Salem, NC (US); Tyler Evans McLawhorn, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 157 days.

(21) Appl. No.: 14/098,714

(22) Filed: Dec. 6, 2013

(65) Prior Publication Data
US 2014/0163317 A1 Jun. 12, 2014

Related U.S. Application Data (60) Provisional application No. 61/734,578, filed on Dec. 7, 2012.

(51) Int. Cl.
*A61B 1/06* (2006.01)
*A61B 1/00* (2006.01)
*A61B 1/05* (2006.01)
*G02B 23/24* (2006.01)
*G02B 6/26* (2006.01)

(52) U.S. Cl.
CPC ....... *A61B 1/00163* (2013.01); *A61B 1/00089* (2013.01); *A61B 1/00096* (2013.01); *A61B 1/05* (2013.01); *G02B 23/2423* (2013.01); *G02B 6/262* (2013.01); *G02B 23/2469* (2013.01); *Y10T 29/49826* (2015.01); *Y10T 156/10* (2015.01)

(58) Field of Classification Search
USPC .......... 600/115–116, 127, 129, 175–177
See application file for complete search history.

(56) References Cited

U.S. PATENT DOCUMENTS

| | | | |
|---|---|---|---|
| 2,102,274 A | 12/1937 | Larimore | |
| 2,843,112 A | 7/1958 | Miller | |
| 3,131,690 A | 5/1964 | Innis | |
| 3,417,745 A | 12/1968 | Edward | |
| 3,866,599 A | 2/1975 | Johnson | |
| 4,201,199 A | 5/1980 | Smith | |
| 4,224,929 A | 9/1980 | Furihata | |
| 4,619,247 A | 10/1986 | Inoue | |
| 4,681,093 A | 7/1987 | Ono | |
| 4,778,247 A | 10/1988 | Carpenter | |
| 5,271,383 A * | 12/1993 | Wilk | A61B 1/00082 600/109 |
| 5,512,035 A | 4/1996 | Konstorum | |
| 5,725,475 A * | 3/1998 | Yasui | A61B 1/00091 600/121 |
| 5,879,369 A * | 3/1999 | Ishida | A61M 25/10 604/96.01 |
| 6,036,685 A * | 3/2000 | Mueller | A61B 1/00098 606/15 |
| 6,193,653 B1 * | 2/2001 | Evans | A61B 17/00008 600/210 |
| 6,953,431 B2 | 10/2005 | Barthel | |

(Continued)

*Primary Examiner* — Matthew J Kasztejna
(74) *Attorney, Agent, or Firm* — Brinks Gilson & Lione (57) ABSTRACT

A flexible lens is mounted to the end of an elongate medical device having a camera, such as an endoscope. The lens is generally solid and is made from a translucent, flexible, and resilient material. In a medical environment, the lens can be pressed against a vessel wall in a patient to enlarge the area viewed by the camera, and can further adapt to the shape of the wall to limit trauma on the patient. When pressed against the vessel wall, the lens can become longitudinally compressed, while becoming wider. The wider and compressed shape of the lens will push blood away from the viewing area to increase the clarity of the camera's field of view.

16 Claims, 5 Drawing Sheets

(56) References Cited

U.S. PATENT DOCUMENTS

| | | | | |
|---|---|---|---|---|
| 7,033,317 | B2* | 4/2006 | Pruitt | A61B 1/00096 600/129 |
| 7,553,278 | B2 | 6/2009 | Kucklick | |
| 7,672,059 | B2 | 3/2010 | Batchko | |
| 8,439,824 | B2* | 5/2013 | Mourlas | A61B 1/00082 600/104 |
| 8,905,921 | B2* | 12/2014 | Titus | A61B 1/00096 600/127 |
| 9,089,258 | B2* | 7/2015 | Goldfarb | A61B 1/0014 |
| 2005/0197530 | A1* | 9/2005 | Wallace | A61B 1/00082 600/116 |
| 2006/0084839 | A1* | 4/2006 | Mourlas | A61B 1/00082 600/116 |
| 2007/0167686 | A1* | 7/2007 | McGrath | A61B 1/00101 600/188 |
| 2010/0286475 | A1* | 11/2010 | Robertson | A61B 1/00096 600/104 |
| 2011/0034774 | A1 | 2/2011 | Doody | |
| 2012/0209074 | A1* | 8/2012 | Titus | A61B 1/00096 600/153 |
| 2012/0232342 | A1* | 9/2012 | Reydel | A61B 1/00082 600/104 |
| 2014/0012079 | A1* | 1/2014 | Koda | A61B 1/00135 600/109 |

* cited by examiner

FLEXIBLE LENS

CROSS-REFERENCE TO RELATED APPLICATIONS

This application claims the benefit of U.S. Provisional Application No. 61/734,578, filed Dec. 7, 2012, which is hereby incorporated by reference in its entirety herein.

BACKGROUND

1. Field of the Invention

The present embodiments relate generally to a flexible external lens for use with an elongate imaging device.

2. Description of Related Art

Using imaging devices to view interior cavities of the human body is common in the medical field. These imaging devices can be elongate and flexible for being passed through a patient's vasculature or other vessel. One such device is an endoscope for performing traditional endoscopic procedures. These devices are generally relatively thin to limit the amount of trauma experienced by a patient when the device is being advanced toward a target viewing site. These devices include a camera disposed at an end of the elongate medical device to allow for viewing at the target viewing site.

Due to the thin and elongate nature of the imaging device, the camera included in the imaging device is also small. The device can include a generally rigid cap at the camera end for protecting the camera from damage due to contact with vessel walls or unintended contact with various parts of the patient's anatomy.

Once positioned near the target viewing site, the elongate and flexible nature of the device allows for the end of the device having the camera to be manipulated or positioned to allow the surgeon to view the interior of the cavity or other vessel. However, the cavity is often filled with blood or other fluid that can obscure the camera's view.

One method for clearing the field of view involves the spraying of a saline or other clear liquid into the area, thereby forcing the blood away from the camera. However, this method is limited in the amount of time that the field of view is clear before the blood or other relatively opaque fluid re-enters the field of view. Moreover, the introduction of the clear fluid may be undesirable in certain medical situations. Additionally, adding a liquid delivery system to the elongate medical device will increase the size of the device, which can increase trauma to the patient during the device's advancement through the body vessel or during the procedure.

Another method for clearing the field of view involves the use of a balloon at the camera end of the device that can be inflated with a clear fluid. When inflated, the balloon will move the opaque fluid in the vessel out of the way. However, the balloon is generally thin to allow for the inflation and deflation, thereby causing it to tend to move side to side, resulting in an inconsistent clear field of view.

Another method involves the use of an elongate and rigid cap on the end of the camera, where the cap is made from a generally transparent material. However, the rigid nature of the cap can result in trauma to the patient in the instance of contact with the vessel wall. Moreover, the rigid cap is generally the same width as the scope to maintain the relatively thin profile of the device. This fixed width limits the width of the clear field of view.

Therefore, there is a need to provide a flexible and elongate imaging device that can maintain a thin profile during advancement through the patient's vasculature that can provide a clear field of view within a body cavity of the patient.

SUMMARY

A lens for mounting to an elongate medical device having a camera is provided, the lens comprising: a lens body having a first longitudinal length extending longitudinally between a proximal end and a distal end, the lens body also having a first width, wherein the lens body is configured for being mounted to an elongate medical device having a camera; a translucent portion of the lens body for creating a field of view for the camera; a tip portion at the distal end of the lens body; a base portion at the proximal end of the lens body, wherein the base portion is sized for being mounted to an elongate medical device having a camera; wherein the lens body has a generally flexible and resilient construction; wherein the lens body has a generally solid cross-section; wherein the lens has a nominal state, in which the lens body has the first length and the first width, and a compressed state, in which the lens body has a second length that is shorter than the first length and second width that is wider than the first width; wherein the lens will transition from the nominal state to the compressed state in response to compression against a barrier and will transition from the compressed state to the nominal state in response to disengagement from the barrier.

In another form, the lens body is made of at least one of a curing adhesive or clear silicone.

In another form, the lens body is generally cylindrical.

In another form, the lens further comprises a shoulder portion extending proximally from the base portion and defining a cavity therein for receiving an elongate medical device.

In another form, the lens material refracts light.

In another form, the tip portion has a generally convex shape.

In another form, the lens further comprises a non-thrombogenic coating.

In one form, a method of viewing a surgical site is provided, the method comprising: providing an elongate medical device having an elongate body having a proximal and distal end and a camera disposed at the distal end, the elongate medical device further including a generally solid, flexible, and resilient translucent lens mounted at the distal end over the camera, wherein the lens has a nominal shape; advancing the elongate medical device through a body lumen of a patient toward a body vessel within the patient; engaging the lens with a vessel wall within the body vessel; and, in response to engaging the lens with the vessel wall, displacing fluids adjacent the lens In another form, the method further comprises, in response to engaging the lens with the vessel wall, adapting the shape of the lens to the shape of the vessel wall so that the lens has a shorter, wider, and compressed shape relative to the nominal shape; retracting the lens from the vessel wall; and in response to retracting the lens from the vessel wall, returning the shape of the lens to the nominal shape from the compressed shape.

In another form, the camera includes a clear field of view through the lens, the field of view having a first length and a first width when the lens is in its nominal shape and having a second length and second width when the lens is in its compressed shape.

In one form, an elongate medical device for visualizing a surgical area is provided, the elongate medical device comprising: a catheter having a body, a proximal end, a distal end, and a lumen extending therebetween having a longitudinal axis; a camera mounted at the catheter distal end; an external lens mounted to the catheter at the catheter distal end, the lens comprising a generally solid and translucent flexible resilient material; wherein the lens is configured to operate in at least two conditions: a first condition where the lens has a nominal shape with a first length and a first width, and a second condition where the lens has a longitudinally compressed shape with a second length and a second width, the second length being shorter than the first length and the second width being wider than the first width; and wherein the lens is further configured to compress into the second condition in response to engagement with an anatomical wall and return to the nominal shape of the first condition in response to retracting away from the anatomical wall.

In another form, the elongate medical device further comprises an accessory channel through the elongate medical device and a needle disposed within the accessory channel.

In another form, the lens is configured to allow the needle to penetrate through the lens.

In another form, the lens is configured to seal against the anatomical wall.

In another form, the lens is made from a curing adhesive material and the lens is mounted to the catheter via adhesive qualities of the curing adhesive material.

In another form, the lens is mounted to the catheter via an adhesive material or via a mechanical connection.

In another form, the lens comprises a generally solid cylindrical body portion and a generally hollow shoulder portion extending proximally from the body portion, and the shoulder portion surrounds a portion of the catheter.

In another form, the catheter portion surrounded by the lens shoulder portion has a smaller width than the remainder of the catheter.

In another form, the elongate medical device further comprises a light source extending along at least a portion of the longitudinal length of the catheter for illuminating areas near the distal end of the catheter.

In another form, the light source includes an illumination end, the illumination end terminates at a shoulder portion extending proximally from a generally cylindrical body portion of the lens body, and the shoulder portion refracts light so that light emitted from the illumination end is refracted and provided at the distal end of the elongate medical device.

In one form, a method for mounting a lens is provided, the method comprising: providing a lens, the lens having a lens body made from a generally solid, translucent, flexible, and resilient material; providing an elongate medical device having a proximal and distal end and a camera disposed at the distal end; mounting the lens to the distal end of the elongate medical device so that the lens covers the camera; wherein the lens is configured to provide a field of view for the camera therethrough in at least two states: a first state where the lens has a first length and a first width, and a second state where the lens has a second length and a second width, the second length being shorter than the first length and the second width being wider than the first width; and wherein the lens is configured to provide the field of view to the camera in the second state in response to a longitudinally compressive force, and further configured to provide the field of view to the camera in the first state in response to being free from a compressive force acting thereon.

In another form, the lens is mounted to the elongate medical device via a mechanical connection.

In another form, the lens is mounted to the elongate medical device via an adhesive connection.

In another form, the adhesive connection is provided by the material of the lens, wherein the lens material is a curing adhesive material.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

Figure 1:
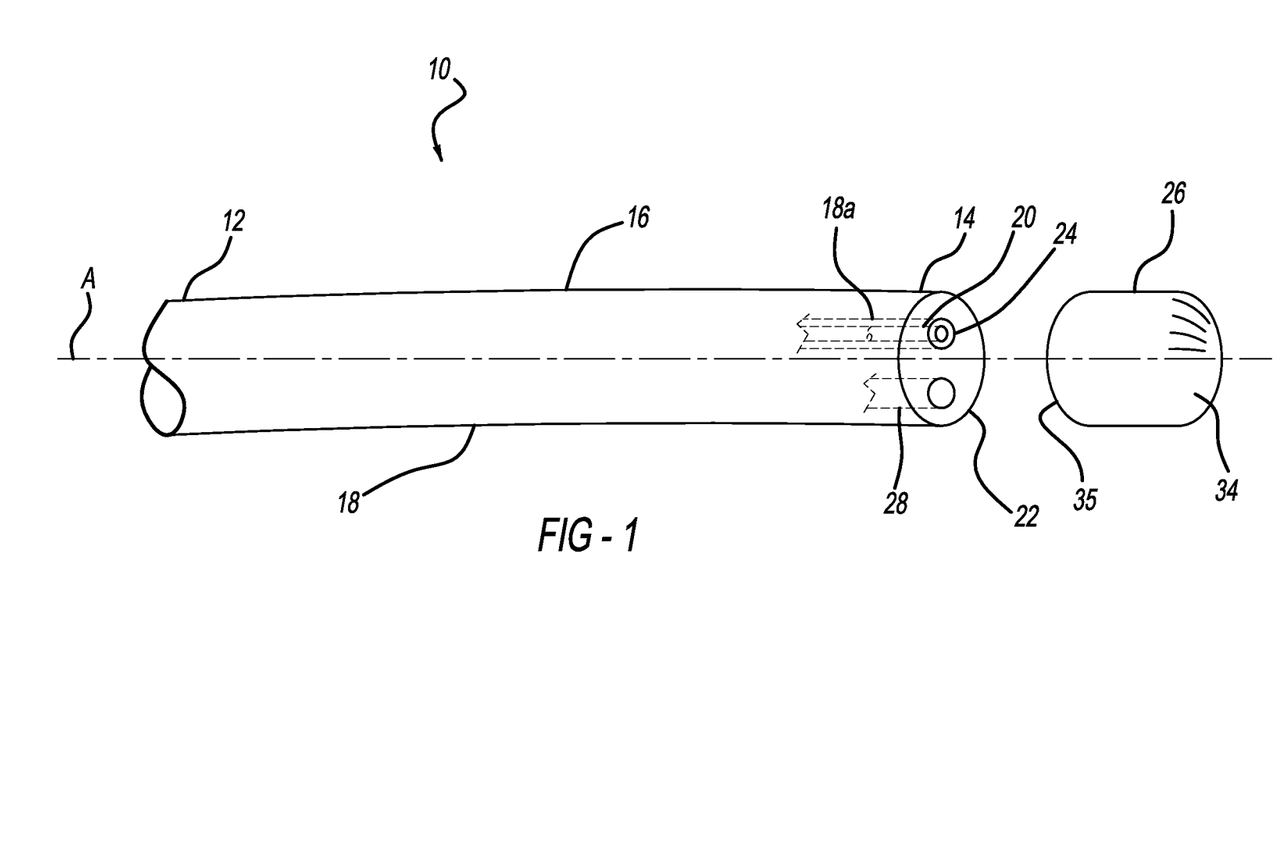
FIG. 1 is an exploded isometric view of a flexible lens and an elongate medical device or endoscope.

Referring now to the drawings, FIG. 1 illustrates an elongate medical device 10 having a proximal end 12 (the end nearest the surgeon in a traditional medical procedure) and a distal end 14 (the end for insertion into the patient in a traditional medical procedure). The elongate medical device 10 includes a longitudinal axis A therealong and can be in the form of a generally flexible endoscope 16.

The structure of a traditional endoscope is known in the art and, therefore, specific detail regarding the general structure and use of the endoscope 16 will not be discussed. Generally, the endoscope 16 includes a catheter or elongate body portion 18 having at least one lumen 18a that extends between the proximal end 12 and the distal end 14. The body portion 18 can have a generally flexible tubular shape for allowing the endoscope 16 to negotiate various body strictures or other tortuous body lumens. The endoscope 16 includes a camera 20 extending through the lumen 18a and mounted at the distal end 14, with the endoscope 16 having a generally flat face 22 at the distal end 14 that includes a viewing port 24 for the camera 20, thereby allowing the camera 20 to provide visual information regarding areas proximate thereto.

The endoscope body 18 can be in the form of a catheter and can have various dimensions and structure known in the art to allow for additional elongate structure or elongate members to extend along the endoscope 16 along with the camera 20.

For example, the endoscope 16 can include a light source 28 for providing light at the distal end 14 thereof. The light source 28 can be elongate, such as a fiber-optic light, and extends along the length of the endoscope 16, preferably within the endoscope 16 along with the camera 20. The fiber-optic light source 28 can include an illumination end 28a at the distal end thereof, where the light source 28 can terminate along the endoscope 16 either at the distal end 14 or at a point proximate the distal end 14, depending on the configuration of other components of the endoscope 16, which will be described in further detail below. The illumination end 28a will, therefore, be disposed near the distal end 14 of the endoscope 16.

In another form, the light source 28 can be in the form of a glow in the dark material, such that the endoscope 16 can be free from the additional elongate light source 28 therealong. By removing the light source 28 from the length of the endoscope 16, the endoscope 16 can have a smaller diameter than if it had the light source 28.

A flexible lens 26 can be mounted to the face 22 of the endoscope 16. The flexible lens 26 can have a nominal shape with a width that conforms to the outer diameter of the endoscope 16. Thus, the flexible lens 26 does not generally overhang the distal end 14 of the endoscope 16 when mounted thereto, thereby permitting the endoscope 16 to maintain a relatively slim profile.

The lens 26 can be made from a flexible, resilient, and generally transparent or translucent material. In one form, the lens 26 can be made from a material known as "Fugitive Glue," which is a proprietary curing adhesive available from FPC Corporation; however, other similarly acting materials could also be used. Fugitive Glue can be formed and cured so that it can adhere to a surface while remaining flexible. In one form, the lens 26 can be adhered to the face 22 of the endoscope 16, while being formed to have its desired shape, as shown in FIG. 1. The flexible and resilient nature of the material of the lens 26 can allow the lens 26 to be pushed against a vessel wall 32 (FIGS. 3 and 9), causing the lens 26 to deform to another shape, adapting and conforming to the vessel wall 32 at the viewing area, while limiting the trauma to the patient. Upon releasing the lens 26 from the vessel wall 32, the resiliency in the material of the lens 26 can allow the lens 26 to return to its original nominal shape for further placement at other areas.

The lens 26 can also be coated with a non-thrombogenic coating, such as heparin, to limit the chance that blood could clot on the lens 26. Limiting the chance of blood clots on the lens 26 assists in ensuring that the lens 26 can provide a generally clear field of view. Of course, it will be appreciated that other types of coatings known in the art could be used on the lens 26 to limit the chance of blood clotting, or for other purposes. Alternatively, the material of the lens 26 can also provide sufficient hemocompatibility such that a coating may not be used.

Figure 2:
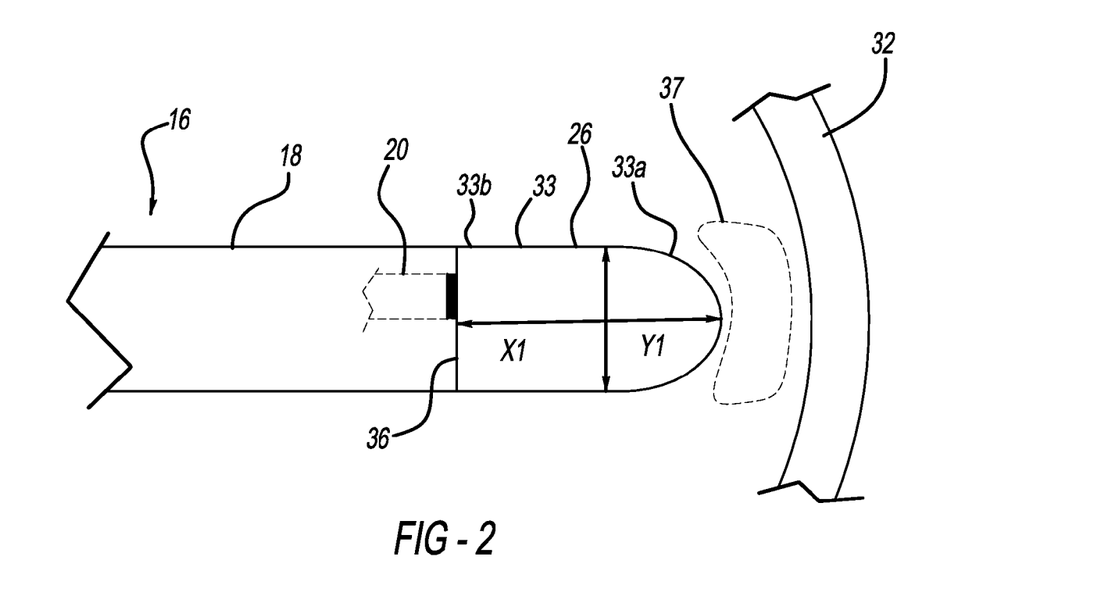
FIG. 2 is a side view of the lens and endoscope located near a vessel wall.

With reference to FIG. 2, as described above, the lens 26 can have a width Y1 that generally corresponds to the width of the endoscope 16. The lens 26 extends a first length X1 from the face 22 of the endoscope 16. In one form, the lens 26 can have a body portion 33 having a tip portion 33a at the distal end thereof and a base portion 33b at the proximal end thereof. The body portion 33 can have a generally solid and cylindrical shape, the tip portion 33a can be in the form of a dome 34 or other convex shape, and the base portion 33b can have a mating surface 35 that is sized to correspond to the endoscope face 22. The shape of the dome 34 operates to assist the endoscope 16 in being negotiated through the tortuous body lumens during insertion of the endoscope 16 into the patient. The shape of the dome 34 also operates to encourage movement of blood 37 to the side of the lens 26 more effectively than if the end of the lens 26 was flat. Of course, other shapes for the tip portion 33a of the lens 26 could also be used, if desired.

Figure 3:
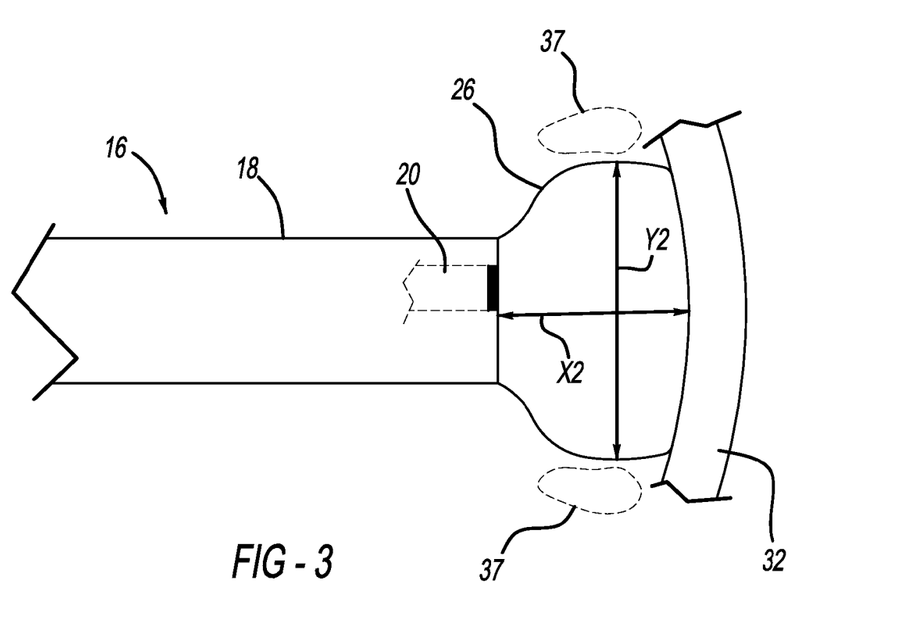
FIG. 3 is another side view of the lens and endoscope pressed against the vessel wall, with the lens in a compressed state.

With reference to FIG. 3, as described above, the flexible and resilient nature of the lens 26 can allow the lens 26 to be compressed in the event that the lens 26 is pushed against the vessel wall 32. The camera 20, being mounted at the distal end 14 of the endoscope 16 can, therefore, be moved closer to the vessel wall 32 when the endoscope 16, and lens 26, are moved toward the vessel wall 32. Thus, the flexible and resilient nature of the lens 26 can allow the surgeon to zoom in on an area by simply compressing the lens 26 against the vessel wall 32. The flexibility of the lens 26 thus provides an advantage over a rigid construction, because a rigid lens is limited by its rigid length in the amount that the camera 20 can approach the wall 32.

When the lens 26 becomes compressed in response to engagement with another surface, such as the wall in a vessel or cavity, the material in the lens 26 will be pushed outward, thereby increasing the width of the lens 26 to width Y2, which is greater than Y1. Thus, the lens 26 can have a compressed shape having a length X2 that is shorter than nominal length X1, along with the wider width Y2, when the lens 26 is pressed against the vessel or cavity wall 32. The shorter and wider shape of the lens 26 while in the compressed state can result in blood 37 outside the lens 26 being pushed aside an additional amount from the field of the view of the lens 26. The clear field of view (generally free from blood) of the camera 20 can generally increase with the width of the lens 26. This can allow for the camera 20 to capture a wider angle free from blood in the field of view due to the increased width of the lens 26.

Figure 4:
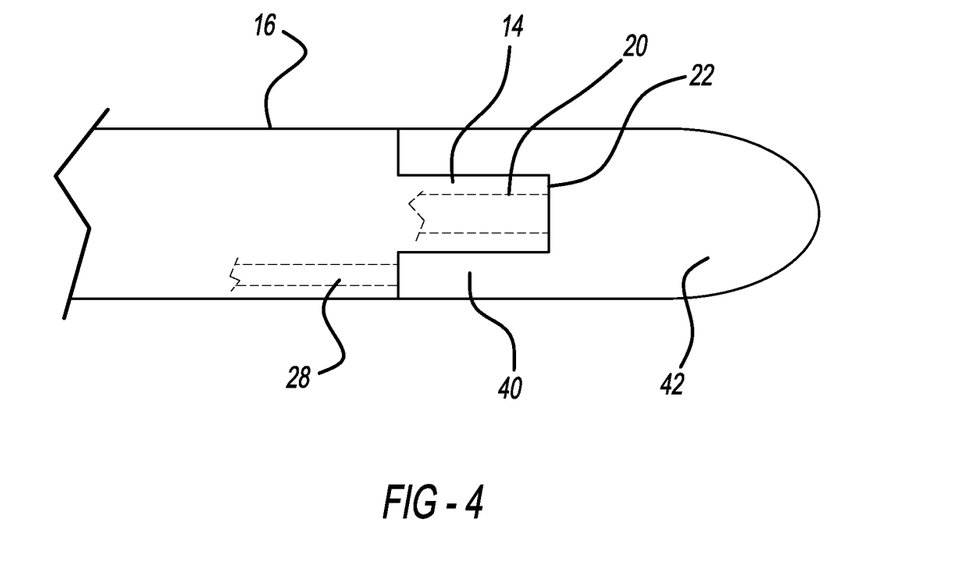
FIG. 4 is a side view of an alternative lens and endoscope.

With reference to FIG. 4, in another form, the lens 26 can be formed or molded around the distal end 14 of the endoscope 16, so that a generally cylindrical portion or shoulder 40 extends around the perimeter of the distal end 14 of the endoscope 16. The shoulder 40 can be generally hollow so that there is a cavity therein. The shoulder 40 can be integral with a major portion 42 of the lens 26. The major portion 42 can resemble the general shape of the previously described lens 26 with respect to length and width. By forming the shoulder 40 around the outside of the distal end 14 of the endoscope 16, the lens 26 can operate to transmit light from an elongate light source 28, such as a fiber optic light source 28, that does not extend the entire length of the endoscope 16. In another approach, the lens 26 with the shoulder 40 can be formed separate from the endoscope 16 for subsequent mounting thereto.

The fiber optic light source 28 can extend along the length of the endoscope 16 as previously described. However, rather than extend fully toward the face 22 of the endoscope 16 as previously described, the light source 28 can terminate at a point proximal from the face 22 of the endoscope 16. The light source 28 can, instead, terminate at a point along the cylindrical shoulder portion 40 of the lens 26.

In this embodiment, the lens 26 can be made from a material that refracts light. Thus, by using such a material, the light source 28 terminating at the cylindrical shoulder portion 40 can illuminate the distal end 14 of the endoscope 16 through the refraction. The refraction of the light through the lens 26 can result in illumination without requiring the light source 28 to extend the entire length of the endoscope 16. Of course, in cases where the light source 28 does extend the entire length, the lens 26 can also be made from a refractive material.

By shortening the length of the elongate light source 28, the portion of the endoscope 16 that is free from a light source 28 therein can be made thinner, thereby reducing the overall profile of the endoscope 16 and increasing the flexibility and maneuverability of the endoscope 16 at the distal end 14, resulting in easier insertion of the endoscope 16 through the body lumen of the patient. FIG. 4 illustrates a schematic representation of this embodiment, and is not to scale. It will be appreciated that the relative lengths of the cylindrical portion 40 and the light source 28 can vary to achieve myriad shapes for the distal end 14 of the endoscope 16.

Figure 5:
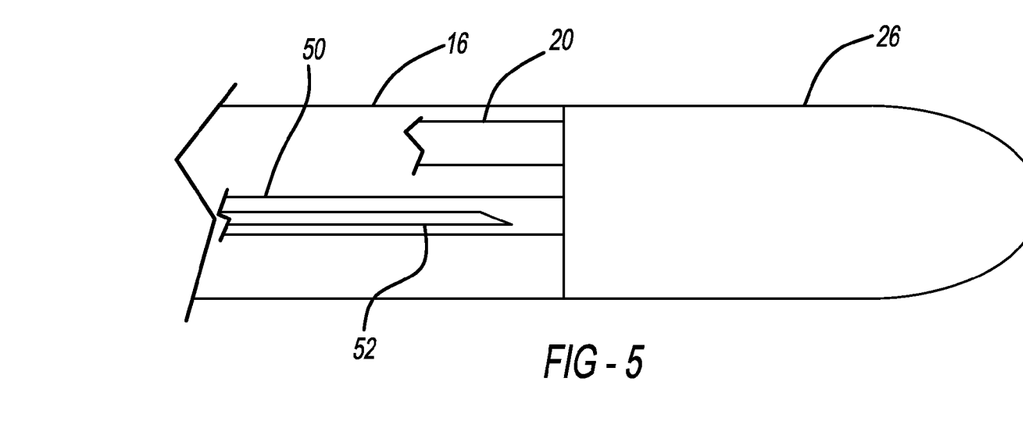
FIG. 5 is a side view of an alternative endoscope having a needle.
Figure 6:
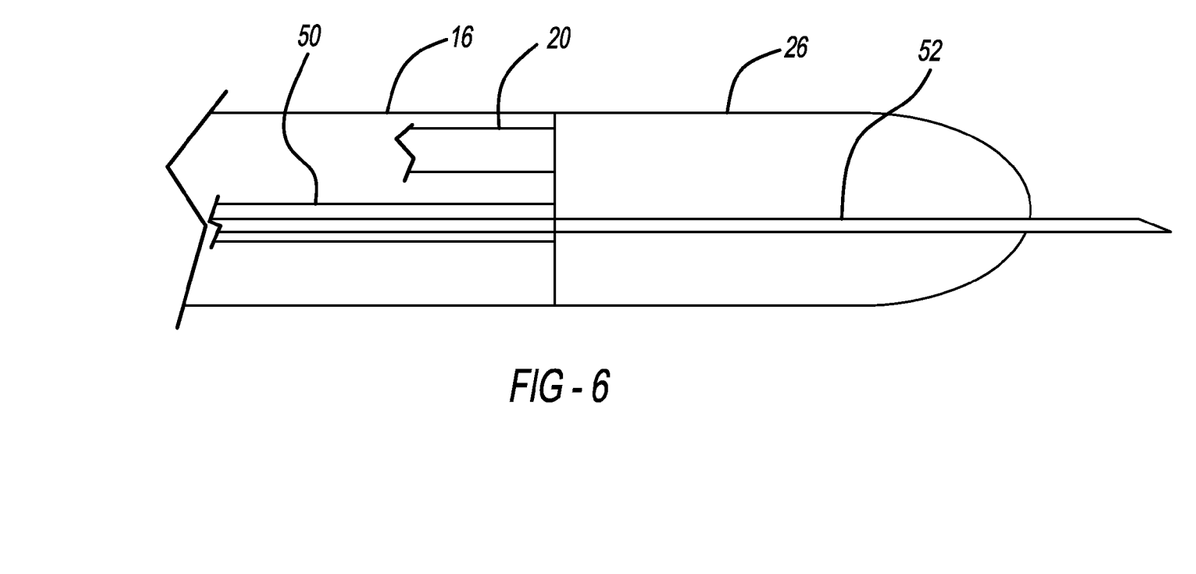
FIG. 6 is a side view of the endoscope of FIG. 5 showing the needle extended through the lens.

With reference to FIGS. 5 and 6, the endoscope 16 can include an accessory channel 50 for allowing a needle 52 to be delivered to the target site. The endoscope 16 can further include additional accessory channels for other needles or other structure for being provided in the endoscope 16. The needle 52 can be advanced through the material of the lens 26 to provide interventional treatment to the target site. The material of the lens 26 will seal off the accessory channel 50 while the needle 52 is extended through the lens 26, and the resilient nature of the material of the lens 26 will also operate to seal off the accessory channel 50 after the needle 52 is retracted back into the endoscope 16. Additionally, the flexible nature of the lens 26 will allow it to provide a seal against the vessel wall at the anatomical site to allow the interventional treatment provided by the needle 52 while limiting or preventing the injected material of the interventional treatment from entering the bloodstream or adjacent areas.

Having described the structure of the lens 26 and elongate medical device 10, or endoscope 16, to which the lens 26 is mounted, the installation and use of the elongate medical device 10 with the lens 26 will now be described.

The elongate medical device 10 or endoscope 16 can be a traditional style endoscope 16 having structure and features generally known in the art. The lens 26 can be adhesively mounted to the end of a traditional endoscope 16 so that the lens 26 covers the face 22 of the endoscope 16, thereby covering the camera 20 and the light source 28. As previously described, the lens 26 can be made from Fugitive Glue, which is itself a cured adhesive material. The Fugitive Glue lens 26 can be formed to the desired shape with the dome 34 at the distal end 14 and then cured so that the lens 26 can be adhesively mounted to the endoscope 16 face 22 via the adhesive qualities of the Fugitive Glue curing adhesive. By installing the lens 26 to a traditional endoscope 16, these endoscopes 16 can be retrofitted with the lens 26 to enhance the viewing capabilities of the traditional endoscope 16. Of course, the lens 26 and endoscope 16 described herein can also be made as a single device, where the endoscope 16 includes the lens 26. In another approach, the lens 26 can be made of a clear silicone material or other translucent material that is flexible and provides a field of view therethrough.

In another form, the lens 26 having the shoulder 40 can be molded around the end of the endoscope 16 so that the lens 26 covers the face 22 as well as the elongate light source 28 when the light source 28 terminates proximal to the endoscope 16 face 22. The lens 26 can be similarly cured to the desired shape.

In another form, the lens 26 can be formed and cured to the desired shape prior to mounting to the endoscope 16. The lens 26 can then be mounted to the endoscope 16 using an additional adhesive material. When the lens 26 is mounted to the face 22 of the endoscope 16, the adhesive is preferably transparent or translucent to allow the camera 20 to maintain a clear field of view. When the lens 26 is mounted around the end of the endoscope 16, the adhesive can be less transparent or translucent if the adhesive is limited to areas on the side of the endoscope 16. In this approach, the adhesive can have sufficient transparency to allow for the light from the elongate light source 28 to be refracted through the lens 26. In the case of a lens 26 made from glow in the dark material, the adhesive for the lens 26 that surrounds the endoscope 16 can be opaque, because it is generally unnecessary for the light to pass through and be refracted by the lens 26. In another approach, the lens can be mounted to the endoscope 16 via a mechanical connection.

Either before or after mounting the lens 26 to the endoscope 16, the lens 26 can be coated with a non thrombogenic material, such as heparin, as previously described. The coating process can be performed along with coating the endoscope 16, if desired, or the coating process can be performed on the lens 26 separate from the endoscope 16. If desired, the lens 26 can be coated while the endoscope 16 remains free from coating, or the endoscope 16 can be coated while allowing the lens 26 to remain free from coating. Alternatively, the lens 26 and endoscope 16 can each be free from coating.

After the lens 26 and endoscope 16 are mounted together and coating is applied, if desired, the endoscope 16 and lens 26 are ready for use. For purposes of discussion, the endoscope 16 and lens 26 together may be described with reference only to the endoscope 16. It will be appreciated that discussion referencing the endoscope 16 can include the lens 26, as well. As the endoscope 16 and lens 26 are coupled together, manipulation of the lens 26 and endoscope 16 are generally linked.

The endoscope 16 is inserted into the patient in a minimally invasive manner known in the art. It will be appreciated, however, that the endoscope 16 described herein could be used in other types of surgery having an increased level of invasiveness. Generally, the surgeon can create a small incision to act as the insertion site, and the endoscope 16 can be inserted into the patient at the location for further travel through the selected body lumen of the patient. The endoscope 16, being flexible, can be fed through the patient's body lumen toward the target site. The flexible nature of the endoscope 16 allows the endoscope 16 to negotiate the tortuous pathway within the body. The surgeon can monitor the progress of the endoscope 16 by viewing images produced by the camera 20, or through other monitoring methods, such as fluoroscopy. It will be appreciated that other manners of tracking the travel of the endoscope 16 known in the art may also be used.

When the endoscope 16 has reached the target area for viewing by the surgeon, the surgeon can determine whether to further adjust the viewing area of the endoscope 16 by manipulating the location of the distal end 14 thereof. Once determining the specific location where viewing is desired, the surgeon can adjust the location of the endoscope 16 so that the camera 20 is directed at that specific location.

Figure 7:
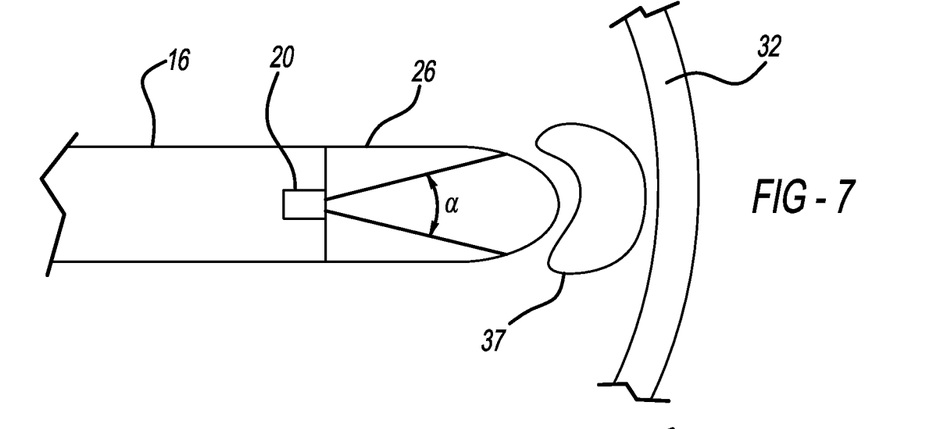
FIG. 7 is a side view of the endoscope and lens in a first position relative to the vessel wall.
Figure 8:
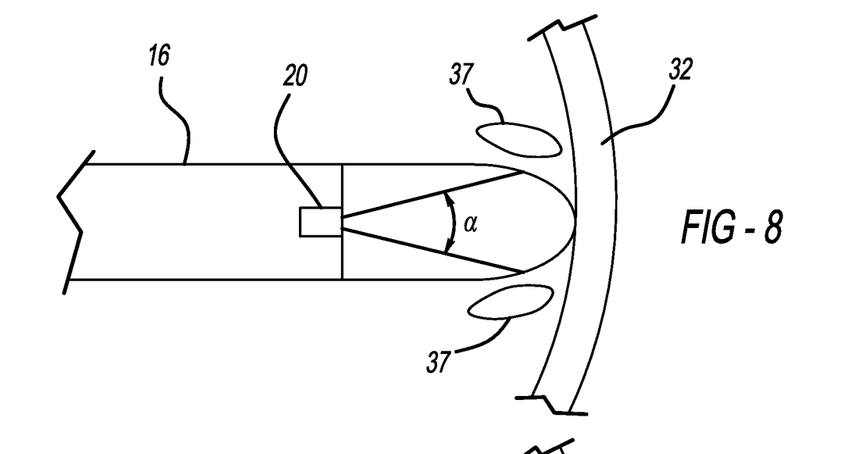
FIG. 8 is a side view of the endoscope and lens in a second position relative to the vessel wall.

With reference to FIGS. 7-9, if blood 37 or other fluid is hindering the view from the camera 20 (FIG. 7), the surgeon can advance the endoscope 16 into the obscured area, thereby forcing the blood 37 out of the area due the lens 26 insertion into the area of the blood 37 (FIG. 8). Blood is generally uncompressible, so by advancing the lens 26 into the area, the blood 37 is forced away, thereby creating a clearer field of view at the end of the lens 26.

If the surgeon desires to view the wall 32 of the particular vessel or cavity where the camera 20 is located, the surgeon can advance the endoscope 16 toward the wall 32, pushing aside the blood 37 in the area (FIG. 8). In addition, the camera 20 will become closer to the desired viewing site, thereby enlarging the area within the field of view α of the camera. The lens 26 can be pressed up against and into engagement with the vessel wall 32, producing a clear view of the vessel wall 32 adjacent the lens 26. The flexible nature of the lens 26 can limit the trauma to the patient in this regard, relative to an endoscope 16 with a rigid lens or other rigid cover.

With the endoscope 16 in engagement with the vessel wall 32, the field of view of the camera 20 toward the intersection of the lens 26 and the vessel wall 32 will be generally clear due to the translucent nature of the lens 26, and the blood being pushed away to accommodate the lens 26 in that space.

Figure 9:
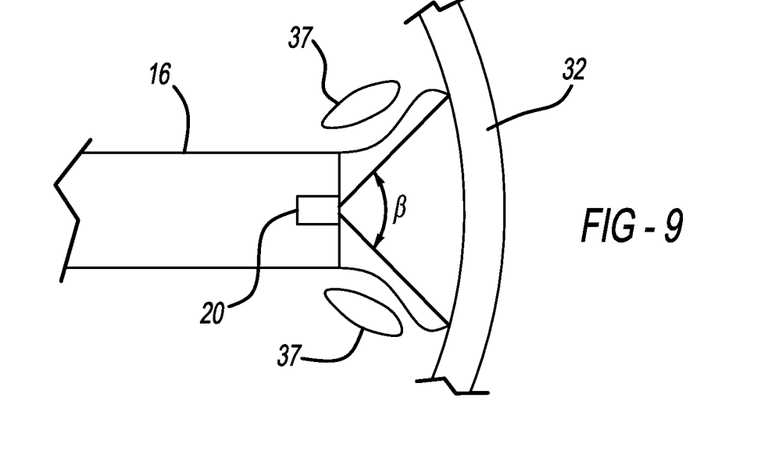
FIG. 9 is a side view of the endoscope and lens in a third position relative to the vessel wall.

The surgeon can further zoom in by pressing the endoscope 16 further toward the vessel wall 32 (FIG. 9). When the endoscope 16 is further pressed against the vessel wall 32, the flexible lens 26 will compress, resulting in a shorter length and greater width. The shorter length allows the for the camera 20 to move closer to the vessel wall 32, thereby producing a larger or more "zoomed-in" image of the vessel wall 32 at the area. In addition to the added detail by zooming in, the added width of the lens 26 caused by the compression results in additional displacement of the blood 37 surrounding the lens 26 relative to the lens 26 being in its nominal shape. The increased width of the lens 26 results in an increased width of the clear portion of the field of view, as indicated by β. Thus, the clear field of view of the camera 20 becomes wider, and the surgeon can view a larger area of the vessel wall 32 free from obstruction by blood or other fluids in the area.

To view another area, the surgeon can withdraw the endoscope 16 away from the vessel wall 32. By withdrawing the lens 26 from the wall, blood and other fluid can re-enter the area vacated by the lens 26, similar to that shown in FIG. 7. The lens 26 will return to its nominal shape due to its resiliency, such that the length of the lens 26 increases and the width decreases relative to the compressed state. The surgeon can then re-position the lens 26 at a different area and can engage another location of the vessel wall 32.

Thus, with reference again to FIGS. 7-9, when the endoscope 16 is positioned as shown in FIG. 7, the camera 20 is a first distance from the vessel wall 32, and the lens 26 is in its nominal state in a first position, with the camera having field of view α. The field of view may be obstructed around the lens and also at the end of the lens due to blood 37. When the endoscope 16 is positioned as shown in FIG. 8, the camera is a second distance from the vessel wall 32 that is shorter than the first distance, and particular features of the wall will be enlarged as viewed through the camera 20 due to it being closer. The lens 26 is still in the nominal shape, but in a second position where the lens 26 is touching the vessel wall 32, thereby displacing the blood 37 away from the front of the lens 26. The field of view α can be generally clear due to the blood 37 being displaced. When the endoscope 16 is positioned as shown in FIG. 9, the camera 20 is a third distance away from the wall that is shorter than the second distance. The features of the vessel wall 32 can be further enlarged as viewed through the camera 20. The lens 26 is in its compressed state in this third position. The field of view β is wider than field of view α, due to the lens 26 having a larger width, and the field of view β can remain clear because of the further displacement of the blood 37.

Upon completing viewing of the area, the surgeon can retract the endoscope 16 from the body in a manner known in the art.

In addition to the imaging of the areas described above, the surgeon can also perform additional medical procedures with the endoscope 16. As described above, the endoscope 16 can include the accessory channel 50 for allowing the needle 52 to be delivered to the target site. To provide surgical treatment with the needle 52, the surgeon can advance the needle 52 through the material of the lens 26. After providing the treatment, the needle 52 can be retracted back through the lens 26 into the accessory channel 50. The flexible and resilient nature of the lens 26, as well as the generally solid cross-section, will seal off the accessory channel 50 after retraction, preventing blood from traveling back into the accessory channel after the treatment. The surgeon can then perform additional treatment with the needle 52 at a different area, if desired. Moreover, when pressing the lens 26 against the vessel wall at the target site, the lens 26 will provide a seal against the vessel wall, which limits or prevents interventional material that is injected by the needle 52 from entering the area surrounding the lens 26, thereby limiting or preventing embolization.

The above described invention has been generally described in relation to an endoscope 16 having a flexible external lens 26 at a distal end 14. However, it will be appreciated that the above concepts can be applied in additional areas. For example, the flexible lens 26 could be used to diagnose plumbing issues or other situations where an elongate camera 20 can be delivered to an area where direct visualization is difficult, or where a minimally invasive technique is desired.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

What is claimed is:

1. A lens for mounting to an elongate medical device having a camera, the lens comprising:
 a lens body having a first longitudinal length extending longitudinally between a proximal end and a distal end, the lens body also having a first width defined by an outermost surface of the lens body when the lens body is in a nominal state, wherein the lens body is configured for being mounted to an elongate medical device having a camera;
 a translucent portion of the lens body for creating a field of view for the camera;
 a tip portion at the distal end of the lens body;
 a base portion at the proximal end of the lens body, wherein the base portion is sized for being mounted to an elongate medical device having a camera;
 wherein the lens body has a generally flexible and resilient construction;
 wherein the lens body has a generally solid cross-section;
 wherein the lens body has the nominal state, in which the lens body has the first length and the first width, and a compressed state, in which the lens body has a second length that is shorter than the first length and second width defined by the outermost surface of the lens body when in the compressed state, wherein the second width is wider than the first width;
 wherein the lens will transition from the nominal state to the compressed state in response to compression against a barrier and will transition from the compressed state to the nominal state in response to disengagement from the barrier;
 wherein the lens body defines a mating surface that defines the proximal end of the lens body and further defining the proximal end of the base portion of the lens body, such that the lens body does not extend proximally beyond the mating surface, the mating surface extending transverse to the longitudinal length of the lens body and having a mating surface outer width defined by an outermost edge of the mating surface, wherein the mating surface outer width corresponds to the first width of the lens body in the nominal state and configured to mate against a distal end of an elongate medical device.

2. The lens of claim 1, wherein the lens body is made of a curing adhesive.

3. The lens of claim 1, wherein the lens material refracts light.

4. The lens of claim 1 further comprising a non-thrombogenic coating.

5. A lens for mounting to an elongate medical device having a camera, the lens comprising:
  a lens body having a first longitudinal length extending longitudinally between a proximal end and a distal end, the lens body also having a first width, wherein the lens body is configured for being mounted to an elongate medical device having a camera;
  a translucent portion of the lens body for creating a field of view for the camera;
  a tip portion at the distal end of the lens body;
  a base portion at the proximal end of the lens body, wherein the base portion is sized for being mounted to an elongate medical device having a camera;
  wherein the lens body has a generally flexible and resilient construction;
  wherein the lens body has a generally solid cross-section;
  wherein the lens body has a nominal state, in which the lens body has the first length and the first width, and a compressed state, in which the lens body has a second length that is shorter than the first length and second width that is wider than the first width;
  wherein the lens will transition from the nominal state to the compressed state in response to compression against a barrier and will transition from the compressed state to the nominal state in response to disengagement from the barrier;
  an elongate medical device for visualizing a surgical area, the elongate medical device comprising:
    a catheter having a body, a proximal end, a distal end, and a lumen extending therebetween having a longitudinal axis;
    a camera mounted at the catheter distal end;
  wherein the lens body is mounted to the catheter at the catheter distal end;
  wherein the elongate medical device further comprises a light source extending along at least a portion of the longitudinal length of the catheter for illuminating areas near the distal end of the catheter;
  wherein the light source includes an illumination end, the illumination end terminates at a shoulder portion extending proximally from a generally cylindrical body portion of the lens body, and the shoulder portion refracts light so that light emitted from the illumination end is refracted and provided at the distal end of the elongate medical device.

6. The lens of claim 5, wherein the elongate medical device further comprises an accessory channel through the elongate medical device and a needle disposed within the accessory channel.

7. The lens of claim 6, wherein the lens body is configured to allow the needle to penetrate through the lens.

8. The lens of claim 5, wherein the lens is configured to seal against the anatomical wall.

9. The lens of claim 5, wherein the lens body is mounted to the catheter via an adhesive material or via a mechanical connection.

10. The lens of claim 5, wherein the lens is made from a curing adhesive material.

11. The lens of claim 10, wherein the lens is attached to the catheter via an adhesive connection provided by the curing adhesive material.

12. A lens for mounting to an elongate medical device having a camera, the lens comprising:
  a lens body having a first longitudinal length extending longitudinally between a proximal end and a distal end, the lens body also having a first width, wherein the lens body is configured for being mounted to an elongate medical device having a camera;
  a translucent portion of the lens body for creating a field of view for the camera;
  a tip portion at the distal end of the lens body;
  a base portion at the proximal end of the lens body, wherein the base portion is sized for being mounted to an elongate medical device having a camera;
  wherein the lens body has a generally flexible and resilient construction;
  wherein the lens body has a generally solid cross-section;
  wherein the lens body has a nominal state, in which the lens body has the first length and the first width, and a compressed state, in which the lens body has a second length that is shorter than the first length and a second width that is wider than the first width;
  wherein the lens will transition from the nominal state to the compressed state in response to compression against a barrier and will transition from the compressed state to the nominal state in response to disengagement from the barrier;
  an elongate medical device for visualizing a surgical area, the elongate medical device comprising a catheter having a body, a proximal end, a distal end, and a lumen extending therebetween having a longitudinal axis;
  wherein the lens body is mounted to the catheter at the distal end of the catheter;
  wherein the lens body comprises a generally solid cylindrical body portion and a generally hollow shoulder portion extending proximally from the body portion, and the shoulder portion surrounds a portion of the catheter;
  wherein the catheter portion surrounded by the lens body shoulder portion has a smaller width than the remainder of the catheter;
  wherein the shoulder portion defines a mating surface at a proximal end thereof, the mating surface extending transverse to the longitudinal length of the lens body, the mating surface mating against the distal end of the catheter.

13. The lens of claim 12, wherein the elongate medical device further comprises a light source extending along at least a portion of the longitudinal length of the catheter for illuminating areas near the distal end of the catheter.

14. The lens of claim 12, wherein the lens is made from a curing adhesive material.

15. The lens of claim 14, wherein the lens is attached to the catheter via an adhesive connection provided by the curing adhesive material.

16. A lens for mounting to an elongate medical device having a camera, the lens comprising:
  a lens body having a first longitudinal length extending longitudinally between a proximal end and a distal end, the lens body also having a first width, wherein the lens body is configured for being mounted to an elongate medical device having a camera;
a translucent portion of the lens body for creating a field of view for the camera;
a tip portion at the distal end of the lens body;
a base portion at the proximal end of the lens body, wherein the base portion is sized for being mounted to an elongate medical device having a camera;
wherein the lens body has a generally flexible and resilient construction;
wherein the lens body has a generally solid cross-section;
wherein the lens body has a nominal state, in which the lens body has the first length and the first width, and a compressed state, in which the lens body has a second length that is shorter than the first length and a second width that is wider than the first width;
wherein the lens will transition from the nominal state to the compressed state in response to compression against a barrier and will transition from the compressed state to the nominal state in response to disengagement from the barrier:
an elongate medical device for visualizing a surgical area, the elongate medical device comprising a catheter having a body, a proximal end, a distal end, and a lumen extending therebetween having a longitudinal axis;
wherein the lens body is mounted to the catheter at the distal end of the catheter;
wherein the lens body comprises a generally solid cylindrical body portion and a generally hollow shoulder portion extending proximally from the body portion, and the shoulder portion surrounds a portion of the catheter;
wherein the catheter portion surrounded by the lens body shoulder portion has a smaller width than the remainder of the catheter;
wherein the elongate medical device further comprises a light source extending along at least a portion of the longitudinal length of the catheter for illuminating areas near the distal end of the catheter;
wherein the light source includes an illumination end, the illumination end terminates at a shoulder portion extending proximally from a generally cylindrical body portion of the lens body, and the shoulder portion refracts light so that light emitted from the illumination end is refracted and provided at the distal end of the elongate medical device.

* * * * *